United States Patent
Bar-Cohen et al.

(10) Patent No.: US 9,393,407 B2
(45) Date of Patent: Jul. 19, 2016

(54) MINIMALLY INVASIVE EPICARDIAL PACEMAKER

(71) Applicants: Children's Hospital Los Angeles, Los Angeles, CA (US); University of Southern California, Los Angeles, CA (US)

(72) Inventors: Yaniv Bar-Cohen, South Pasadena, CA (US); Gerald Loeb, South Pasadena, CA (US); Michael Silka, La Canada, CA (US); Ramen Chmait, La Crescenta, CA (US)

(73) Assignees: Children's Hospital Los Angeles, Los Angeles, CA (US); University of Southern California, Los Angeles, CA (US)

( * ) Notice: Subject to any disclaimer, the term of this patent is extended or adjusted under 35 U.S.C. 154(b) by 0 days.

(21) Appl. No.: 14/390,943

(22) PCT Filed: Apr. 5, 2013

(86) PCT No.: PCT/US2013/035377
§ 371 (c)(1),
(2) Date: Oct. 6, 2014

(87) PCT Pub. No.: WO2013/152259
PCT Pub. Date: Oct. 10, 2013

(65) Prior Publication Data
US 2015/0088221 A1    Mar. 26, 2015

Related U.S. Application Data

(60) Provisional application No. 61/620,701, filed on Apr. 5, 2012.

(51) Int. Cl.
*A61N 1/05*     (2006.01)
*A61N 1/375*    (2006.01)
(Continued)

(52) U.S. Cl.
CPC .............. *A61N 1/0587* (2013.01); *A61N 1/059* (2013.01); *A61N 1/362* (2013.01); *A61N 1/375* (2013.01);
(Continued)

(58) Field of Classification Search
CPC ... A61N 1/0587; A61N 1/362; A61N 1/3787; A61N 1/37205; A61N 1/375; A61N 1/3756; A61N 1/372; A61N 1/378
See application file for complete search history.

(56) References Cited

U.S. PATENT DOCUMENTS

RE28,990 E  * 10/1976  Hon ..................... A61B 5/0408
                                                600/376
4,166,470 A  *  9/1979  Neumann ............ A61B 5/0031
                                                607/33
(Continued)

FOREIGN PATENT DOCUMENTS

WO    WO2010104952    9/2010
WO    WO2010141929    12/2010

OTHER PUBLICATIONS

International Search Report and Written Opinion, WO2010141929, Oct. 29, 2010.
(Continued)

*Primary Examiner* — Brian T Gedeon
(74) *Attorney, Agent, or Firm* — Latimer IPLaw, LLC

(57) ABSTRACT

A fully implantable cardiac pacemaker system is provided. The pacemaker system includes a pacemaker having an electrode sub-assembly containing an electrode and a base into which the electrode is embedded. It also includes an implantable package that has electronic components for providing electrical pulses to a patient's heart. The pacemaker also has a power supply and a flexible electrically conductive lead that connects the electronic components to the electrode. In addition to the pacemaker, the pacemaker system includes a removable insertion casing that is physically attached to the base portion of the electrode sub-assembly. Upon insertion of the pacemaker into a patient's heart, the pacemaker is detached from the removable insertion casing and deployed fully in the patient's chest. The pacemaker system has particular use in fetal applications.

21 Claims, 7 Drawing Sheets

(51) Int. Cl.
*A61N 1/372* (2006.01)
*A61N 1/362* (2006.01)
*A61N 1/378* (2006.01)

(52) U.S. Cl.
CPC ............ *A61N 1/3756* (2013.01); *A61N 1/3787* (2013.01); *A61N 1/37205* (2013.01); *Y10T 29/49002* (2015.01)

(56) References Cited

U.S. PATENT DOCUMENTS

| | | | |
|---|---|---|---|
| 5,680,859 | A | 10/1997 | Urion et al. |
| 6,185,464 | B1 | 2/2001 | Bonner et al. |
| 2001/0029362 | A1 | 10/2001 | Sirhan et al. |
| 2005/0222633 | A1 | 10/2005 | Edvardsson |
| 2006/0009827 | A1 | 1/2006 | Kurth et al. |
| 2007/0016276 | A1 | 1/2007 | Heil et al. |
| 2008/0140139 | A1 | 6/2008 | Heinrich et al. |
| 2009/0082827 | A1 | 3/2009 | Kveen et al. |
| 2011/0106233 | A1 | 5/2011 | Morgan et al. |
| 2011/0307043 | A1 | 12/2011 | Ollivier |
| 2012/0004667 | A1 | 1/2012 | Reddy et al. |
| 2012/0078267 | A1 | 3/2012 | Bar-Cohen et al. |

OTHER PUBLICATIONS

International Search Report and Written Opinion, WO2013152259, Jul. 12, 2013.
International Search Report and Written Opinion, WO2014182948, Nov. 20, 2014.

* cited by examiner

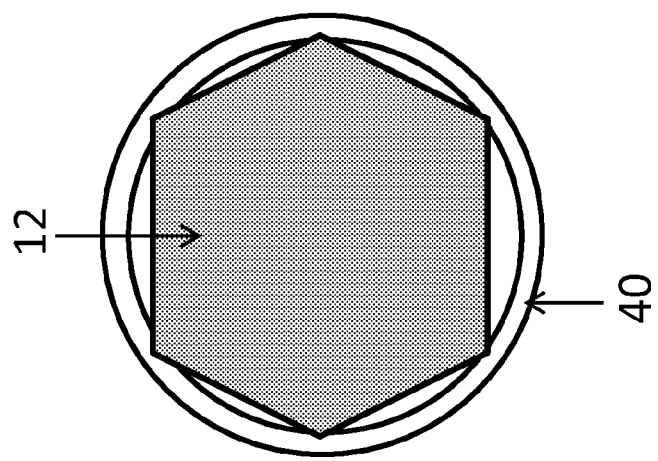

MINIMALLY INVASIVE EPICARDIAL PACEMAKER

CROSS-REFERENCE TO RELATED PATENT APPLICATIONS

This application relies on and claims the benefit of the filing date of U.S. provisional patent application No. 61/620,701, filed 5 Apr. 2012, the entire disclosure of which is hereby incorporated herein by reference.

STATEMENT OF GOVERNMENT INTEREST

This invention was made with government support under grant numbers UL1-RR031986 and R01-HD075135-01 awarded by the National Institutes of Health—CTSI. The government has certain rights in the invention.

BACKGROUND OF THE INVENTION

1. Field of the Invention

The present invention relates to the field of medical devices. More specifically, the present invention relates to cardiac pacemakers and assemblies containing them for use in epicardial implantation.

2. Description of Related Art

Complete heart block in the fetus is a life-threatening emergency with no effective treatment options beyond watchful waiting. Fetal bradycardia due to heart block can be persistent in utero, and hydrops fetalis can develop in more than a quarter of these pregnancies. Once hydrops fetalis occurs, if the fetus cannot be delivered due to prematurity or other clinical concerns, fetal demise is nearly inevitable.

Due to the often severe consequences of fetal heart block, various treatment options have been undertaken in an effort to treat these fetuses. Pharmacologic therapy has been trialed, usually with administration of medications to the mother with anticipated placental passage of the agent to the fetus. Because damage to the fetal cardiac conduction system is believed to be due to maternal autoimmune antibodies in many of these cases, fluorinated steroids have been used to prevent or reverse the heart block. Studies on this therapy, however, have demonstrated unclear, if any, benefit from these agents. Intravenous gammaglobulin has also been administered to these patients in an attempt to reverse or halt progression of the immunologic damage, but results of this therapy have also been disappointing. Beta-adrenergic agents are known to increase heart rates in children and adults, but maternal administration of these agents results in heart rate increases that have not been proven to affect overall survival.

When a newborn, child, or adult presents with symptomatic complete heart block, treatment usually consists of implantation of a pacemaker to ensure an adequate heart rate. With appropriate pacing, these patients are usually asymptomatic with an excellent prognosis. Similar benefits would be expected from pacing a fetus with complete heart block, theoretically allowing resolution of hydrops in 1-2 weeks and permitting an otherwise normal gestation. A conventional pacemaker would then be implanted at delivery. Over the last two decades, several investigators have attempted to place pacemakers in a fetus. To date, however, there have been no survivors of fetal pacing. Previous approaches have relied on the placement of a pacing wire on the fetal heart with an extra-uterine pulse generator implanted in the mother. This has inevitably failed because of lead dislodgement due to fetal movement.

U.S. patent application publication number 2012/0078267, which is incorporated herein by reference, discloses a pacemaker device and device assembly. The pacemaker device is disclosed as having an electrode for connecting the device to fetal heart tissue. The electrode is attached to a relatively short wire or lead that connects the electrode to a power source located on the proximal end of the device. The pacemaker device further comprises a coil retention mechanism that retains the lead within a recess in the body of the pacemaker device until the pacemaker device is deployed in a patient. The coil retention mechanism is held in contact with the body of the pacemaker device by a "holder", which can be a string, thin wire, or elastic band that runs along the sides and across the distal end of the pacemaker device. The pacemaker device can be provided as part of a device assembly, which includes the pacemaker device and a "pusher", which is in essence a rod or rod-like element that can be used to implant and deploy the pacemaker device into cardiac tissue. The pusher is held in contact with the pacemaker device by the holder. In use, the pacemaker device is implanted into cardiac tissue through force applied on the pusher (e.g., by rotating the pusher about its central axis to impart a twisting motion to a screw-like electrode, resulting in implantation of the electrode into cardiac tissue). Once the pacemaker is implanted, the holder is cut and removed, thus allowing the lead to extend from the pacemaker device body, and the pusher to be removed from the pacemaker device. While the device and device assembly represent a significant advancement in the art, and in particular for treatment of fetuses, improved technologies would advance the pacemaker art.

SUMMARY OF THE INVENTION

The present invention provides a completely intra-thoracic pacemaker that can be used for pacing of a heart in need of external pacing. Although the pacemaker can be designed for use in any patient, due to its novel design, it advantageously can have an unusually small size, which is well suited for use in fetuses. In its various embodiments, the pacemaker can be designed, and thus appropriately sized, for fetuses, neonates, infants, children, or adults. For the purposes of brevity, the present disclosure focuses at times on embodiments relating to a fetal pacemaker. However, it is to be understood that the concepts discussed can be equally applied to pacemakers sized for other patient groups. The pacemaker is a self-contained, single-chamber pacemaker that can be percutaneously implanted into a human without exteriorized leads. The pacemaker thus allows for fetal movement after implantation without significant risk of electrode dislodgement. Fortunately, with successful fetal pacing, a complete recovery from hydrops fetalis can now be expected with survival to term and a nearly normal life.

In one aspect, the invention provides a minimally-invasive epicardial pacemaker system. The system generally includes: A) a pacemaker comprising i) an electrode sub-assembly comprising an electrode connected to and partially encased by a base, ii) an implantable package with electronic circuitry and a power supply, and iii) a flexible, electrically conductive lead connecting the electrode to the implantable package; and B) a tubular removable insertion casing directly contacting at least a portion of the base of the electrode sub-assembly, wherein contact provides sufficient physical connection between the insertion casing and the base to permit an operator to apply axial motion, rotational motion, or both, to the electrode via force applied directly or indirectly to the insertion casing. More specifically, the base is defined by a proximal surface, a distal surface, and an exterior surface, while the tubular removable insertion casing is defined by a proximal surface, and distal surface, an inner or interior surface, and an outer or exterior surface. Attachment of the base and the removable insertion casing is by way of physical contact of at least a portion of the outer surface of the base with at least a portion of the inner surface of the removable insertion casing. In some embodiments, the system further includes: C) a push rod that contacts the proximal end of the pacemaker (typically the power supply) to allow force to be applied to the pacemaker, resulting in release of the pacemaker from the removable insertion casing. The implantable package of the pacemaker can comprise a water-impermeable shell surrounding the electronic circuitry and at least a portion of the power supply, which protects, at least to some extent, the circuitry from contact with water. In embodiments, the pacemaker of the system further includes a water-resistant material, such as a water-resistant polymer, which is in contact with and coats electronic circuitry that is susceptible to damage by contact with water. In these embodiments, at least during fabrication, and preferably as part of the final pacemaker product, the water-impermeable shell surrounds the electronic circuitry and retains the water-resistant material in the area around the circuitry. As would be envisioned by the skilled artisan, the electronic circuitry of the implantable package typically comprises electronic components for providing controlled electrical pulses from the pacemaker to a patient's heart. In exemplary embodiments relating to fetal uses, the removable insertion casing has an outer diameter or width of 3.3 mm or less. In exemplary embodiments relating to non-fetal use, the removable insertion casing typically has an outer diameter or width of 3 mm to 8 mm.

In another general aspect, the invention provides a minimally-invasive epicardial pacemaker. In general, the pacemaker includes a body having the following parts: i) an electrode sub-assembly comprising an electrode connected to and at least partially encased by a base defined by a proximal surface, a distal surface, and an outer surface, ii) an implantable package with electronic circuitry and a power supply, and iii) a flexible, electrically conductive lead connecting the electrode to the implantable package. The implantable package can also comprise a water-impermeable shell surrounding at least a portion of the power supply and all of the electronic circuitry, which protects, at least to some extent, the circuitry from contact with water. In embodiments, the pacemaker further comprises a water-resistant material, such as a water-resistant polymer, which is in contact with and coats electronic circuitry that is susceptible to damage by contact with water. In these embodiments, at least during fabrication and preferably as part of the final pacemaker product, the entire airspace within the water-impermeable shell is taken up by the water-resistant material. Further, in these embodiments, at least during fabrication and preferably as part of the final pacemaker product, the water-impermeable shell retains the water-resistant material in the area around the circuitry. In embodiments, the shell is permanently affixed to the power supply, such as by attaching it to the outer surface of the power supply. A portion of the outer surface of the power supply may be left exposed outside the shell, where it may function as a return electrode, completing the circuit for stimulation current emitted by the electrode that is located in the heart muscle. In exemplary embodiments relating to the pacemaker in an un-deployed state, no part of the electrode sub-assembly is housed in any portion of the implantable package.

In yet another general aspect, the invention provides a process for making a minimally invasive cardiac pacemaker. In general, the method includes: physically connecting an electrode encased in part by a base to a flexible, electrically conductive lead; physically connecting the flexible lead to electronic circuitry for controlling the pacing of a pacemaker; physically connecting the electronic circuitry to a power supply; and physically connecting a water-impermeable shell to the power supply such that the shell surrounds at least a portion of the power supply and all of the electronic circuitry. In some embodiments, the method further comprises coating the electronic circuitry with a protectant comprising a water-resistant material, such as a water-resistant polymer, to coat electronic circuitry that is susceptible to damage by contact with water. In preferred embodiments, the entire airspace within the water-impermeable shell is filled with the water-resistant material. In some embodiments, the step of connecting the shell to the power supply includes permanently affixing the shell to the power supply, for example by way of a water-resistant adhesive that bonds the inner surface of the shell to the outer surface of the distal end of the power supply. In other embodiments, the shell is removed after the electronic circuitry is coated by the water-resistant material and no physical support for the water-resistant material is needed.

In an additional aspect, the present invention provides a process for making a minimally invasive cardiac pacemaker system. In general, the method includes: physically connecting an electrode encased in part by a base to a flexible, electrically conductive lead; physically connecting the flexible lead to electronic circuitry for controlling the pacing of a pacemaker; physically connecting the electronic circuitry to a power supply; physically connecting a water-impermeable shell to the power supply such that the shell surrounds at least a portion of the power supply and all of the electronic circuitry, and encasing the power supply, electronic circuitry, flexible lead, and at least a portion of the base in a tubular removable insertion casing, wherein the removable insertion casing physically and directly contacts at least a portion of the base, and wherein contact provides sufficient physical connection between the insertion casing and the base to permit an operator to apply axial motion, rotational motion, or both, to the electrode via force applied directly or indirectly to the insertion casing. The base is attached to the removable insertion casing at the distal end of the removable insertion casing such that only the electrode (partially or wholly) or the electrode and part of the base, extend beyond the distal end of the removable insertion casing. In some embodiments, the method further comprises inserting a push rod into the proximal end of the removable insertion casing, wherein the push rod is sufficiently long to contact the pacemaker on its distal end and remain outside the removable insertion casing on its proximal end. In embodiments, the method further comprises coating at least a portion of the electronic circuitry with a protectant comprising a water-resistant material, such as a water-resistant polymer, to coat electronic circuitry that is susceptible to damage by contact with water. In preferred embodiments, the entire airspace within the water-impermeable shell is filled with the water-resistant material. In embodiments, the method additionally comprises permanently affixing the water-impermeable shell to the power supply, for example by way of an adhesive. In other embodiments, the shell is removed after the electronic circuitry is coated by the water-resistant material and no physical support for the water-resistant material is needed.

In yet a further aspect, the invention provides a method of using the pacemaker system of the invention to deploy a minimally-invasive epicardial pacemaker into cardiac tissue of a patient. Broadly speaking, the method can be considered a method of treating a patient in need of an artificial pacemaker or a method of implanting an artificial pacemaker into a patient. The method generally comprises contacting epicardial heart tissue with the tip of the pacemaker system of the invention, specifically by way of contact of the electrode and the heart tissue; implanting the electrode into the heart tissue; disconnecting the pacemaker from the removable insertion casing; and removing the removable insertion casing from the patient's body. Typically, the method further comprises, prior to contacting of the electrode to the heart tissue, inserting a cannula into the chest cavity of the patient to provide access to the heart tissue. Further, typically the heart is monitored for pacing provided by the implanted pacemaker. Process steps for implantation of the pacemaker can be followed using any known technique, including fiber optic visualization, use of non-invasive radiation (e.g., real-time X-ray imaging, etc.), ultrasound, and the like.

BRIEF DESCRIPTION OF THE DRAWINGS

The accompanying drawings, which are incorporated in and constitute a part of this specification, illustrate exemplary embodiments and features of the invention, and together with the written description, serve to explain certain principles of the invention. The drawings are not intended as a limitation of the invention, but instead are provided to give the reader a better understanding of certain details of embodiments of the invention.

DETAILED DESCRIPTION OF EXEMPLARY EMBODIMENTS OF THE INVENTION

Figure 1:
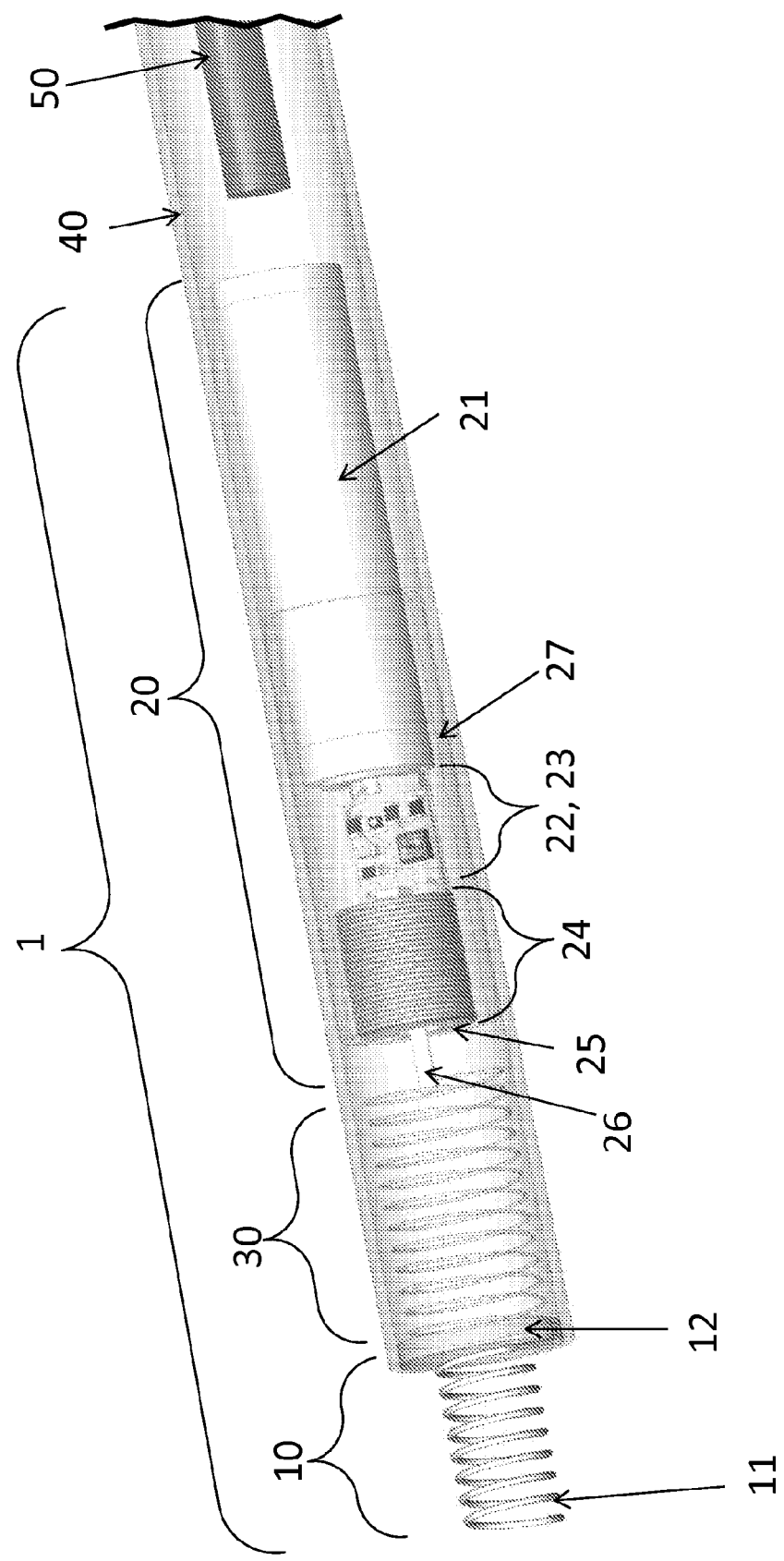
FIG. 1 shows an embodiment of a pacemaker system of the invention in a form ready for use.

Reference will now be made in detail to various exemplary embodiments of the invention. It is to be understood that the following discussion of exemplary embodiments is not intended as a limitation on the invention, as broadly disclosed herein. Rather, the following discussion is provided to give the reader a more detailed understanding of certain aspects and features of the invention.

Before embodiments of the present invention are described in detail, it is to be understood that the terminology used herein is for the purpose of describing particular embodiments only, and is not intended to be limiting. Further, where a range of values is provided, it is understood that each intervening value, to the tenth of the unit of the lower limit, unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither, or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which the term belongs. Although any methods and materials similar or equivalent to those described herein can be used in the practice of the present invention, the preferred methods and materials are now described. All publications mentioned herein are incorporated herein by reference to disclose and describe the methods and/or materials in connection with which the publications are cited. The present disclosure is controlling to the extent it conflicts with any incorporated publication.

As used herein and in the appended claims, the singular forms "a", "an", and "the" include plural referents unless the context clearly dictates otherwise. Thus, for example, reference to "a pulse" includes a plurality of such pulses and reference to "the electrode" includes reference to one or more electrodes and equivalents thereof known to those skilled in the art, and so forth. Furthermore, the use of terms that can be described using equivalent terms include the use of those equivalent terms. Thus, for example, the use of the term "patient" is to be understood to include the terms "human", "subject", and other terms used in the art to indicate one who is subject to a medical treatment.

The present invention provides a single-chamber heart pacing device (i.e., pacemaker) that is self-contained and can be percutaneously implanted without exteriorized leads. The device is applicable to all patients in need of heart pacing. However, the device is particularly advantageous for use in a fetus because the lack of exteriorized leads permits subsequent fetal movement without risk of dislodgement of the electrode. Such a design is now possible because of significant developments in pacemaker microtechnology and advances in fetal surgical intervention, allowing the pacing device to be percutaneously deployed, for example through the maternal abdomen, under ultrasound guidance or other imaging techniques known in the art.

It is estimated that at least 500 pregnancies in the United States are affected by fetal heart block annually. These pregnancies may be candidates for the present device. The device of the invention provides an extremely effective treatment option for a population of fetuses that would either die in utero or require premature delivery with all of its co-morbid consequences.

The device of the invention takes advantage of the commercial availability of many of the components that make up the device. As such, the invention addresses the key anatomical, physiological, and surgical issues required in designing a pacemaker while using off-the-shelf electronic components. The use of off-the-shelf electronics also provides adaptability to the device, extending its usefulness to a much broader population, including not just fetuses, but also newborns, infants, and even adults with limited venous access. As battery technology inevitably improves, this novel pacemaker design could replace standard single-chamber pacemaker techniques with implantation of the entire pacing system into the patient's thorax via a minimally invasive technique.

The pacemaker can be extremely small compared to current commercially-available pacemakers, and can be designed for implantation through a narrow (3.3 mm) cannula directly into the fetal chest. Such a pacemaker is referred to herein at times as a "micro-pacemaker". For fetal use, the cannula can therefore be inserted directly through the maternal abdomen via a trocar without the need for surgical incisions in the mother or fetus and without the need to significantly disrupt the fragile amniotic sac. Furthermore, the needles, trocars, and cannulas used for percutaneously accessing the fetal myocardium through the maternal abdomen are already available, and procedures requiring similar access to the fetal chest are performed successfully, safely, and routinely by those of skill in the art. An exemplary embodiment of the micro-pacemaker has been designed to fit through these already-available surgical tools.

The present pacemaker also takes advantage of the limited requirements for longevity and programmability to enable use of simple, high efficiency, low-cost electronic design and fabrication. In embodiments, it also takes advantage of the most recent advances in transcutaneous inductive power transmission, such as used on advanced neural prosthetic devices, to allow the tiny lithium cell of the pacemaker to be recharged from outside the patient, or in fetal applications, the patient and mother, as needed during gestation.

As discussed above, in one aspect, the invention provides a minimally-invasive epicardial pacemaker system. The system generally includes a pacemaker according to the invention and a removable insertion casing, which are physically in contact with each other during storage and implantation of the pacemaker, but which are disconnected during deployment of the pacemaker into a patient. The process of disconnecting the pacemaker from the removable insertion casing is achieved through the use of force applied to the pacemaker by a push rod, which expels the pacemaker from the removable insertion casing. In embodiments, the push rod is included as part of the pacemaker system.

A pacemaker according to the invention comprises three basic electrical components, which are physically and electrically connected in the following order: i) an electrode sub-assembly, ii) a flexible, electrically conductive lead, and iii) an implantable package. The pacemaker can also comprise a water-resistant and/or water-impermeable barrier that is attached to, and can be considered a part of, the implantable package, and which surrounds at least a portion of the implantable package.

The electrode sub-assembly includes two elements: i) an electrically conductive electrode, and ii) a base into or onto which the electrode is physically attached. The electrode can be made of any electrically conductive material, including but not limited to metals and metal alloys. Those of skill in the art are aware of suitable electrode materials, and the practitioner is free to select any suitable material desired. In exemplary embodiments, the electrode comprises iridium. Further, a portion of the electrode can be treated, using standard techniques known and routinely practiced in the art, to render a portion of it non-conductive. In exemplary embodiments, the treatment comprises a vapor-deposited coating of a polymer of chloroparaxylylene, known as Parylene-C. Yet further, the electrode can have any suitable size and shape for implanting into heart tissue. Those of skill in the art are aware of the various sizes and shapes for electrodes that have been shown to be suitable for attaching pacemakers, and in particular pacemaker electrodes, to heart tissue via implantation of electrodes into the heart tissue. Various commercially available electrodes are known to the skilled artisan and can be obtained easily without the need to design and fabricate new electrodes. In exemplary embodiments, the electrode is in the shape of a corkscrew, spiral, coil, or other shape that can be inserted into cardiac tissue using a twisting or spinning motion. It is advantageous for the exposed portion of the electrode through which the stimulation pulse will be applied to encompass a sufficient number of heart muscle cells so that the electrical activity thereby elicited in those heart muscle cells can spread effectively to the remainder of the ventricles.

The base of the electrode sub-assembly is provided mainly for two functional reasons. First, it provides a physical platform that mechanically stabilizes the electrode during implantation of the electrode into cardiac tissue. And second, it provides a physical element for attaching a removable insertion casing (discussed in more detail below) to the pacemaker. The base thus is made of a material that is selected in conjunction with the material from which the removable insertion casing is made. In general, the two materials are selected to interact with each other such that they stay physically connected with sufficient strength to permit an operator to apply axial motion, rotational motion, or both, to the electrode via force applied directly or indirectly to the removable insertion casing. Yet, the strength must not be so great that the base and the removable insertion casing cannot be separated to deploy the pacemaker. As the skilled artisan will recognize, the amount of force required to implant an electrode into cardiac tissue is relatively small. Therefore, the strength of the attachment between the base and the removable insertion casing is also relatively small, and the operator should be able to separate the two using average human strength. In exemplary embodiments, the base is made of epoxy, such as in the form of an epoxy disk, and one end of the electrode is embedded in the epoxy, while the removable insertion casing is made of Grilamid® L25 (EMS-Chemie AG, Switzerland), a high-viscosity, UV-stabilized, extrusion grade nylon 12, or other tough polymer such as nylon or Teflon® (E. I. Du Pont De Nemours and Co., Delaware). In this case, the disk is relatively rigid and the casing is relatively deformable. In another exemplary embodiment, the disk is a silicone elastomer and the casing is made of metal. In that case, the casing is relatively rigid and the disk is relatively deformable.

The electrode is partially embedded in, encased in, or otherwise covered by material of the base. Its protruding portions are preferably partially or wholly insulated in those regions not expected or desired to make contact with the heart muscle or the flexible lead. In exemplary embodiments, this insulation is a vapor-deposited layer of Parylene-C, which is masked from covering those parts of the electrode that are intended to supply the electrical pulses to the myocardium and, where necessary, to connect to the flexible lead. However, it is not critical how the insulation is applied and/or the ends of the electrode exposed to allow for conduction of electricity, and the practitioner is free to select any suitable method. To allow for a physical and electrical connection between the electrode and the flexible lead, the proximal tip of the electrode is exposed on the proximal side of the base. For ease of fabrication, typically the proximal tip of the electrode is aligned, with respect to the proximal surface of the base, such that the proximal tip of the electrode extends beyond the proximal surface of the base. However, one could also achieve an exposed electrode tip by forming the base with the electrode embedded, then removing base material to expose the proximal tip of the electrode.

In addition to the electrode sub-assembly, the pacemaker of the invention includes an implantable package. The implantable package includes: i) electronic circuitry and ii) a power supply. Among other possible uses, the electronic circuitry provides electronic components for providing controlled electrical pulses from the pacemaker to a patient's heart. As mentioned above, an advantage of the present pacemaker design is that it can be fabricated completely or to a great extent using commercially-available, off-the-shelf components and common techniques for making electrical connections among the various components. Thus, the skilled artisan would readily be able to obtain suitable electronic components (e.g., a printed circuit board) for use in the implantable package and connect them to a lead, a power supply, and any other components of the pacemaker, for example by soldering the components to make physical and electrical connections.

In one preferred embodiment, the electronic circuitry is a relaxation oscillator that produces stimulation pulses with preset parameters of amplitude, duration, and rate that depend on the values of the resistors and capacitors that comprise the circuitry. Advantageously, the rate of pulsing generated by a relaxation oscillator varies according to the voltage of its power supply. The pulses can be detected by electrodes placed on the surface of the mother's abdomen and the rate measured to monitor the state of charge of the power supply. Alternatively, the electronic circuitry can be constructed entirely or in part by a custom integrated circuit, in which case the stimulation pulses can have programmable parameters that are transmitted to and stored in the implanted pacemaker or that are computed by digital logic circuitry in the pacemaker according to various sensing and pacing algorithms that are well-known in the art. The electronic circuitry can include means to measure and transmit information to an external receiver concerning the state of charge of the power supply. In any of these embodiments, the small size of the pacemaker limits the amount of electrical charge that can be stored in the power supply. Thus, it is advantageous to incorporate into the electronic circuitry means to capture and to store energy that can be transmitted from an external transmitter in order to recharge the power supply as needed to maintain functioning of the pacemaker.

The implantable package also includes a power supply. The pacemaker of the invention can be powered by commercially-available power supplies, as are known in the art. In exemplary embodiments, the power supply includes a lithium ion cell. Preferably, it is a rechargeable lithium ion cell that can provide power for 2-3 weeks of pacing before needing to be recharged. The ion cell can be recharged periodically, for example weekly, from outside the body, including the body of a pregnant woman, the charging system being based on designs already used for transcutaneously powered neural stimulators, such as the Battery-Powered BION (BP-BION®, Boston Scientific Inc.).

In view of the fact that the power supply can be rechargeable, in some embodiments the implantable package further comprises components for receiving power from an external source. For example, the implantable package can comprise a receiving coil for electromagnetic or mechanical recharging of the device. The implantable package can also comprise components for storing power and/or releasing power. It thus can further comprise an output capacitor and a metallic post, such as one comprising platinum, connecting the output capacitor to the flexible lead. Yet further, it can comprise a relaxation oscillator. Thus, charging/recharging of the power supply can be effected through the use of mechanical energy.

In the design of the pacemaker, the end of the power supply not connected to the electronics is exposed to the environment of the patient's chest cavity. It thus functions to complete the electrical circuit using the patient's body.

Because the pacemaker will be exposed to an aqueous environment while functioning, and because the electronic circuitry will not function properly in, and/or will be degraded by, such an environment, the electronic circuitry must be protected from contact with water. As such, the implantable package includes a water barrier to protect the electronic circuitry. One way to provide such a barrier is to encase the electronic circuitry in a water-impermeable shell (e.g., comprising glass, metal, ceramic, etc.) that is closed on one end and open on the other, the open end being slid over the electronic circuitry and physically connected, by way of a water-tight connection or hermetic seal, to the outside surface of the power supply, thus creating a water-free environment for the electronic circuitry. A water-tight or hermetic feedthrough can be used to make a water-tight connection between the lead on the outside and the electronic circuitry on the inside of the impermeable shell, typically at the distal end of the shell. Attachment of the feedthrough to the lead and to the electronics can be accomplished using any suitable technique, such as by soldering, brazing, or welding, for example by using electromagnetic (e.g., laser or other optical wavelength energy, or ultraviolet energy) or ultrasound energy focused on the connection point, as is well-known in the art.

In addition or alternatively, the electronic circuitry can be covered, encased, encapsulated, or otherwise coated in a protective material that is water-resistant. The water-resistant material can be any material that slows the movement of water from the patient's body to the electronic circuitry Alternatively, the water-resistant material may protect the electronic circuitry from the deleterious effects of water by forming an adhesive bond with the surfaces of the electronic circuitry, thereby preventing water vapor that diffuses through most materials from condensing on the surfaces. In embodiments, the water-resistant material is a water-resistant polymer, such as epoxy, a silicone elastomer, a liquid crystal polymer, polyethylene, high-density polyethylene, polystyrene, expanded polystyrene, bulk-polymerized polystyrene, or acrylate polymers.

The electronic circuitry can be coated in any way desired by the practitioner, including molding, dipping, brushing, spraying, and vapor deposition. In exemplary embodiments, the electronic circuitry is coated using a process whereby the circuitry is first surrounded by an open-ended tubular shell, which extends lengthwise from the power supply to beyond the point where the circuitry is located. In some embodiments, the tube makes a water-tight seal with the power supply, whereas in other embodiments, a seal is formed as a result of water-resistant material filling voids between the tube and the power supply. The tube is then filled (e.g., using a vacuum applied at the battery to draw the material into the tube) with a water-resistant material, or a material that, when polymerized, is water resistant, such that the material fills the airspace within the tube. Once the material is in a physically stable form (e.g., it has polymerized to a solid state), the shell can be removed by sliding it off of the power supply. However, to better protect the electronic circuitry from exposure to water, in embodiments, the shell is a water-impermeable shell (e.g., comprising glass, metal, ceramic) and it is left on the power supply such that it permanently surrounds the electronic circuitry and retains the water-resistant material in the area around the circuitry. Thus, in embodiments, the implantable package comprises a water-impermeable shell, a water-resistant material, or both. In exemplary embodiments, the implantable package comprises a polymerized encapsulant contained within a water-impermeable shell.

Accordingly, the invention provides a novel packaging system intended to protect the circuitry from bodily fluids, which is a significant improvement over currently available technologies in this field. In essence, the packaging system includes the use of a protective coating, such as a polymeric material, to encase electronic components that are susceptible to damage (e.g., short-circuiting, corrosion) by water. The protective coating and electronic components are further surrounded by a water-impermeable shell. The polymer, the shell, and the placement of the sensitive electronics within the pacemaker and in relation to other components of the pacemaker are combined to reduce the surface area at which water can enter the implantable package of the pacemaker and increase the distance any water that has entered the pacemaker must travel before contacting the sensitive electronics.

As discussed elsewhere herein, to deploy the pacemaker, physical force is used to eject the pacemaker from the removable insertion casing. As can be seen with reference to FIG. 1, the force from a push rod applied to the proximal side of the power supply (the right side of the pacemaker in FIG. 1 and FIG. 2) is translated to a force applied to the base element of the electrode sub-assembly of the pacemaker by way of physical contact between the electronics and the flexible lead. Although this is a suitable way to effect deployment of the pacemaker, in preferred embodiments, an additional element is provided in the implantable package to alter the contact point for the electronic circuitry from the flexible lead to the base element of the electrode sub-assembly itself. Such a configuration reduces possible damage to the lead. The additional element, also referred to herein as a deployment spacer, can be made of any suitably hard material to effect transfer of force from the electronic circuitry to the base element of the electrode sub-assembly. However, to better protect the electronic circuitry from exposure to water, it is preferred that the deployment spacer comprise a water-resistant material, such as one discussed above. Advantageously, the deployment spacer can be configured so as to provide mechanical support and electrical insulation for the connection between the flexible lead and the electronic circuitry.

The deployment spacer can be provided in any suitable shape that functions to apply force to the implantable package, such that when the implantable package is in physical contact with the base element of the electrode sub-assembly, the force is transmitted through the implantable package to the base element. It thus may be in the form of a platform (for contact with the electronic circuitry) with a projection (for contact with the base element of the electrode sub-assembly) that fits within the inner space formed by coils of the flexible lead. Alternatively, the deployment spacer comprises the projecting end of a rod that provides a physical and electrical connection between the flexible lead and the electronic circuitry. The connection between the rod and the flexible lead can be over-coated with a protective coating material to provide mechanical support and electrical insulation of this connection.

The pacemaker of the invention, in addition to the electrode sub-assembly and the implantable package, includes a flexible, electrically conductive lead. The flexible lead has two ends: one end is physically and electrically connected to the implantable package while the other end is physically and electrically connected to the electrode sub-assembly, and in particular, the electrode. The flexible, electrically conductive lead can be made of any suitable flexible material that conducts electricity, and in particular a sufficient amount of electricity in pulses to pace a human heart. The lead is flexible, but preferably is stiff enough to retain a general shape. For example, the lead can be in the form of an expanded spring, which can be deformed to allow for compression while in an un-deployed state, but also allow for re-expansion upon deployment of the pacemaker in a patient's chest. The expanded spring can be encased in a highly elastic material, such as a silicone elastomer, in order to prevent ingrowth of connective tissue. The flexibility of the lead allows for movement of the electrode relative to the implantable package to accommodate cardiac and respiratory motion. Typically, the flexible lead comprises one or more metals or alloys of metals, as known in the art. In exemplary embodiments, the present design uses an alloy comprised of 80% platinum and 20% iridium to achieve the desired combination of elasticity and stiffness. Typically, the flexible lead is coated by, or otherwise further comprises, an insulative material around the electrically conductive material(s) along much of the length of the lead to prevent transmission of electricity except from the implantable package to the electrode. In an exemplary embodiment, this insulative material is a vapor-deposited layer of Parylene-C. The present design uses a lead that is designed to span only the distance from the heart to the chest cavity (e.g., about 2-10 mm in its extended form for fetal applications or, for child, adolescent, or adult applications, about 10-50 mm in its extended form).

It is to be noted at this point that the practitioner may elect to extend the base of the electrode sub-assembly such that it covers not only a portion of the electrode, but a portion of the flexible lead as well. Implementation of the pacemaker design in such a fashion is suitable as long as attachment of the pacemaker to the removable insertion casing via the electrode sub-assembly is retained. In other words, reference herein to a base within the context of the electrode sub-assembly includes embodiments where the base is designed as part of the lead. The important feature is that the pacemaker, as a whole, includes a base element that functions to physically attach the pacemaker to the removable insertion casing in a detachable way.

In summary, in exemplary embodiments, the minimally-invasive epicardial pacemaker of the invention includes a body having the following parts: i) an electrode sub-assembly comprising an electrode at least partially encased by a base, ii) an implantable package comprising electronic circuitry that is at least partially protected from damage by water by a water-resistant and/or water impermeable material, and a power supply, and iii) a flexible, electrically conductive lead connecting the electrode to the implantable package. In embodiments, the implantable package comprises a water-impermeable shell that surrounds at least the electronic circuitry. In embodiments, the implantable package comprises a water-resistant material, such as a water-resistant polymer, which is in contact with and coats electronic circuitry that is susceptible to damage by contact with water. In embodiments, the implantable package comprises both.

As discussed above, in addition to the pacemaker, the pacemaker system of the invention includes a tubular removable insertion casing. The removable insertion casing physically contacts at least a portion of the base of the electrode sub-assembly, which results in non-permanent attachment of the pacemaker to the removable insertion casing. The physical contact provides a sufficient physical connection between the inner surface of the insertion casing and the outer surface of the base to permit an operator (e.g., a cardiac surgeon) to apply axial motion, rotational motion, or both, to the electrode of the pacemaker via force applied directly or indirectly to the removable insertion casing. The physical contact between the base and the casing further provides a physical connection that can be broken (i.e., the removable insertion casing can be detached, disconnected, removed, etc. from the base) through the use of normal human force, such as by using a thumb to push a rod against the proximal end of the pacemaker.

There are numerous ways to provide the appropriate physical connection between the removable insertion casing and the base, some of which are illustrated in FIG. 3 and discussed below. A non-limiting example includes the use of friction to create a non-permanent attachment. For example, both the base and the removable insertion casing can have a circular cross-sectional shape, where the diameter of the outer surface of the base is the same as, or larger than, the diameter of the inner surface of the removable insertion casing. Inserting the base into the removable insertion casing during production/ fabrication of the system results in a friction fit that holds the two elements in physical contact. As another example, the inner diameter of a circular removable insertion casing can be slightly smaller than the outer diameter of a base, where either one or both of these elements is deformable. Insertion of the base into the removable insertion casing causes the base to deform inwardly, the removable insertion casing to deform outwardly, or both, thus providing a friction fit. While a circular cross-section was exemplified, the reader should understand that any geometrical shape, including without limitation, triangular, square, pentagonal, hexagonal, or octagonal, can be used. Yet again, the inner surface of the removable insertion casing can be of a different cross-sectional shape than the outer surface of the base. The two are designed in conjunction such that, at certain points on the surface of each piece, one or both pieces deform to create a friction fit. For example, a removable insertion casing with an internal circular cross-section of 3 mm can be combined with a base having a hexagonal (or any other non-circular shape, such as another polygonal shape) external cross-section with a vertex-to-vertex length of 3.1 mm. Insertion of the base into the removable insertion casing will cause the removable insertion casing, the base, or both to deform at the areas where the vertices of the base contact the inner surface of the removable insertion casing.

Stated another way, in embodiments, the removable insertion casing has an inner surface that contacts the base, the base has an outer surface that contacts the removable insertion casing at its inner surface, and the cross-sectional shape defined by the inner surface of the removable insertion casing is different than the cross-sectional shape defined by the outer surface of the base such that the removable insertion casing and base make contact at some, but not all, points on their respective surfaces. Upon inserting the base into the removable insertion casing, material from the base, the removable insertion casing, or both deforms to create a friction fit.

Any number of other combinations of removable insertion casing and base shapes can be envisioned by the skilled artisan to provide a suitable attachment scheme. For example, a raised feature can be disposed on the inner surface of the removable insertion casing to make contact with the outer surface of the base (or vice versa); a raised feature can be disposed on the inner surface of the removable insertion casing and a notch can be cut into the outer surface of the base to receive the raised feature (or vice versa). In essence, any imperfection in either surface that causes the two surfaces to contact can be introduced.

As discussed above, the material from which the removable insertion casing is fabricated is often selected in conjunction with the material from which the base is made in order to create a physical connection that allows the removable insertion casing to be used to impart motion to the electrode of the pacemaker yet also allows for facile separation of the removable insertion casing from the base. Examples of materials from which the removable insertion casing can be made are provided above.

Figure 3A:
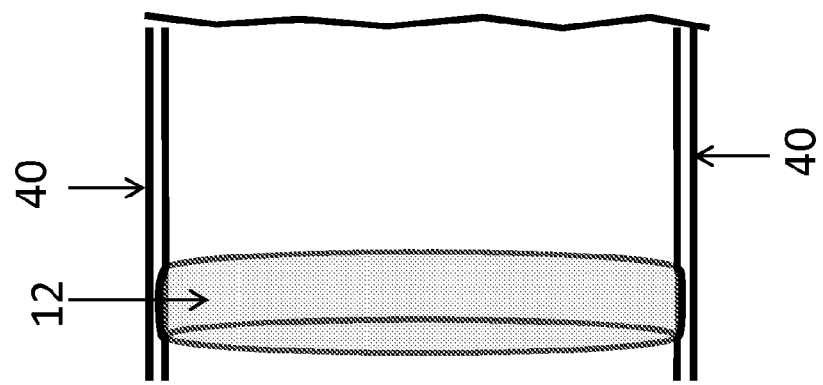
FIG. 3, Panels A-C, show details of various preferred embodiments for retaining the pacemaker electrode within the removable casing in a form ready for use and deployment.
Figure 3C:
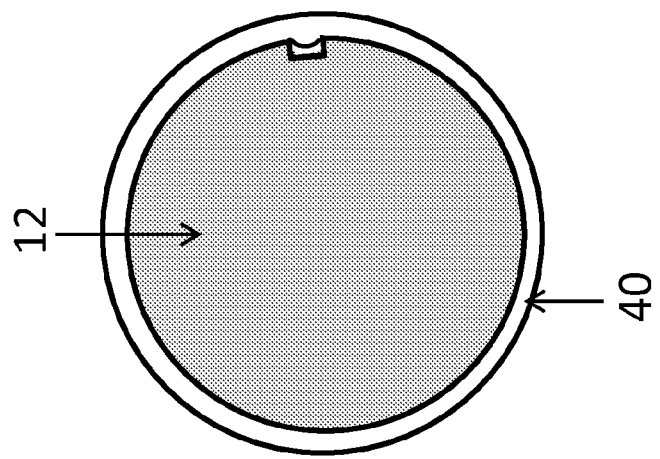

Turning now specifically to FIG. 3, it can be seen that various ways are possible to effect the detachable connection desired between base 12 and removable insertion casing 40. In the preferred embodiment depicted in FIG. 3A as a side view, base 12 is comprised of a substantially rigid material, such as epoxy. Base 12 is illustrated after being forced into the end of removable insertion casing 40, which has a slightly smaller inside diameter than the outside diameter of base 12, and is comprised of a more elastic material, such as polyamide. Advantageously, base 12 is forced a short distance past the distal end of removable insertion casing 40 so that it is effectively captured on both sides by the distorted walls of removable insertion casing 40. In an alternative embodiment depicted as a front view in FIG. 3B, base 12 has a polygonal shape and size such that its vertices distort the cylindrical shape of removable insertion casing 40 when forced into its end. In yet another exemplary alternative embodiment, depicted in FIG. 3C, base 12 has a notch that corresponds to and accommodates an asperity from the inside wall of removable insertion casing 40. These embodiments and other mechanical means that would be obvious to increase or control the axial and rotational forces that can be resisted by the detachable connection between base 12 and removable insertion casing 40 are included within the scope of this invention.

While not limited to any particular size or cross-sectional shape, in general, the removable insertion casing and the pacemaker are designed to fit within the inner diameter of a cannula that is suitable for use in surgery for the patient of interest. As such, typically, the removable insertion casing has an external, or outer, size and shape that defines a circular cross-section that can fit within a pre-selected cannula for the patient of interest. For fetal applications, in general the removable insertion casing has a diameter of about 4 mm or less, such as from 4 mm to 1 mm, for example 4 mm, 3 mm, 2 mm, or 1 mm. Likewise, in general the removable insertion casing has a length of about 20 cm-30 cm or more for fetal applications. In general, for child and adult applications, it is possible to use a larger surgical cannula, thus permitting a larger power supply that can sustain a pacing function for a longer period without requiring recharging. In that case, the removable insertion casing can have a diameter of about 4 mm to 12 mm or less, and a length of that required to traverse the insertion track from the skin surface to the heart of the patient, which will vary from about 5 cm to 30 cm depending on the point of entry. The practitioner may select any particular value falling within these ranges based on various considerations. In exemplary embodiments relating to fetal uses, the removable insertion casing has an outer diameter or width of 3.3 mm or less. In exemplary embodiments relating to non-fetal use, the removable insertion casing typically has an outer diameter or width of approximately 5 mm, 8 mm, or 12 mm, corresponding to the diameters of standard ports used in minimally invasive surgery.

It is to be noted that, as mentioned above, geometric shapes other than circular for the outer surface of the removable insertion casing are encompassed by the invention as long as they fit in the cannula selected for use in a particular implementation of the invention. Likewise, the external surface of the pacemaker is pre-defined such that the entire pacemaker fits in, and can be expelled from, a pre-defined removable insertion casing. That is, the skilled artisan will immediately recognize and factor in alterations needed to implement the invention in geometric shapes other than those having circular cross-sections.

As discussed at other places in this document, to deploy the pacemaker in a patient, the pacemaker must be detached from the removable insertion casing. This can be accomplished in any number of ways, but in exemplary embodiments, force is applied to the proximal end of the pacemaker to expel it from the removable insertion casing. As such, in some embodiments, the pacemaker system of the invention further includes an element, referred to herein as a push rod, that contacts the proximal end of the pacemaker (typically the power supply) to allow force to be applied to the pacemaker, resulting in release of the pacemaker from the removable insertion casing. The push rod can be made of any suitably hard material that can transmit a physical force from the practitioner, either directly or indirectly, to the proximal end of the power supply.

Suitable materials include any number of materials known in the art for use in medical procedures, including, but not limited to, plastics, glass, ceramics, and metals. In preferred embodiments, the push rod is made of a material that can be sterilized, such as by autoclave or irradiation. The skilled artisan will appreciate that the length of the push rod will be at least sufficient to, when employed, cause deployment of the pacemaker from the removable insertion casing.

In addition to the pacemaker and pacemaker system, the invention provides a process for making a minimally invasive cardiac pacemaker and pacemaker system. In general, the method includes: physically connecting an electrode to a flexible, electrically conductive lead; physically connecting the flexible lead to electronic circuitry for controlling the pacing of a pacemaker; physically connecting the electronic circuitry to a power supply; and placing a water barrier around electronic circuitry that is susceptible to damage by water. The method also includes creating a base that surrounds a portion of the electrode. In embodiments, the water barrier comprises a water-resistant material, such as a water-resistant polymer, and the step of placing a water barrier around electronic circuitry comprises applying the water-resistant material onto the electronic circuitry, as described above. In embodiments, the water barrier comprises a water-impermeable material, such as glass, ceramic, or metal, and the step of placing a water barrier around electronic circuitry the method comprises placing a water-impermeable shell around at least the electronic circuitry. In exemplary embodiments, the shell is attached to the exterior surface of the power supply by way of a water-tight connection. In these embodiments, the exterior surface of the battery can be considered as part of the water-impermeable shell. In embodiments where both a water-impermeable shell and a water-resistant material are used, the shell can function to retain the water-resistant material in the area around the circuitry. In embodiments, the method additionally comprises permanently affixing the shell to the power supply, for example by way of an adhesive.

In addition to being physically connected, the electrode, lead, electronics, and power supply are also electrically connected such that electrical energy from the power supply can travel to the electrode tip to provide electrical pulses to the patient's heart. Any known way to make physical and electrical connections can be used in the present methods, including, but not limited to, soldering, brazing, welding, crimping, and conductive polymers.

Where the method is practiced for making a minimally invasive cardiac pacemaker system, the method comprises physically attaching a removable insertion casing to the base of an electrode sub-assembly of the invention such that at least a portion of the inner surface of the removable insertion casing physically contacts at least a portion of the outer surface of the base to provide a sufficient physical connection between the removable insertion casing and the base to permit an operator to apply axial motion, rotational motion, or both, to the electrode via force applied directly or indirectly to the removable insertion casing. In some embodiments, the method includes: encasing the power supply, electronic circuitry, flexible lead, and at least a portion of the base of a pacemaker of the invention in a tubular removable insertion casing. In some embodiments, the method further comprises inserting a push rod into the proximal end of the removable insertion casing, wherein the push rod is sufficiently long to contact the pacemaker on its distal end and remain outside the removable insertion casing on its proximal end.

In exemplary embodiments, the pacemaker of the invention comprises an electrode that has at least its tip in the shape of a corkscrew. To implant such a pacemaker into cardiac tissue, force is applied, either directly or indirectly, to the removable insertion casing to allow for axial or rotational motion, which allows the practitioner (e.g., a cardiac surgeon) to screw the electrode into the cardiac tissue. By "directly", it is meant that the practitioner physically directly touches the removable insertion casing and imparts the axial force. By "indirectly", it is meant that the practitioner does not physically directly touch the removable insertion casing, but instead causes rotation of the removable insertion casing through a separate handle or mechanical device. For example, the removable insertion casing can be attached to a pistol-like device in which pulling of a trigger by the practitioner causes rotation of the removable insertion casing. Additionally, a handle could be attached to the proximal end of the device and allow easier rotation of the casing.

In summary, embodiments of the invention include a process for making a minimally invasive cardiac pacemaker assembly, where the method comprises: physically connecting an electrode encased in part by a base to a flexible, electrically conductive lead; physically connecting the flexible lead to electronic circuitry for controlling the pacing of a pacemaker; physically connecting the electronic circuitry to a power supply; and encasing the power supply, electronic circuitry, flexible lead, and at least a portion of the base in a removable insertion casing, wherein the removable insertion casing physically contacts at least a portion of the base, and wherein contact provides sufficient physical connection between the insertion casing and the base to permit an operator to apply axial or rotational motion to the electrode via force applied to the insertion casing.

One general aspect of the invention is a method of using the pacemaker system of the invention to deploy a minimally-invasive epicardial pacemaker into cardiac tissue of a patient. The method generally comprises: contacting epicardial heart tissue with the electrode of the pacemaker system of the invention; implanting the electrode into myocardial tissue; disconnecting the pacemaker from the removable insertion casing; and removing the removable insertion casing from the patient's body. Typically, the method further comprises, prior to contacting of the electrode to the heart tissue, inserting a cannula, by way of a trocar, into the chest cavity of the patient to provide access to the heart tissue. However, the method can be practiced as part of an open-chest surgery procedure by targeting atrial myocardium.

The method of the invention contemplates implanting an electrode into either or both of the ventricular myocardium and atrial myocardium. For fetal applications, pacing via ventricular myocardium is mandatory. However, even in a fetus, an atrial pacemaker can be useful for terminating certain arrhythmias (supraventricular tachycardia). The invention thus encompasses implantation of multiple, such as two, independently placed epicardial pacemakers that communicate with each other. Such a configuration is desirable and even necessary for many pediatric and adult applications. Technology for implantation of multiple electrical stimulation devices that communicate are known in other fields, as exemplified by U.S. Pat. Nos. 7,593,776, 6,175,764, 6,051, 017, and 5,571,148 (all of which are incorporated herein by reference in their entireties), as well as in a journal article by Sachs, N. A. and Loeb, G. E. ("Development of a BIONic muscle spindle for prosthetic proprioception.", IEEE Trans. Biomedical Engineering, 54(6):1031-1041, June, 2007; incorporated herein by reference in its entirety). In embodiments, two pacemaker devices of the invention are implanted, the first is implanted into the atrium and the second into the ventricle. Communication can be from the atrial device to the ventricle device or the other way around. For example, the atrial device can send a signal when it senses or paces the atrium and the ventricular device can then detect the signal and pace the ventricle at a predefined time after the atrial event. This results in "DDD" pacing, whereby atrial contraction is followed by ventricular contraction and results in the most optimal cardiac physiology. Dual-pacing in this manner is accomplished in embodiments by having the ventricular device sense the stimulus artifact from the atrial device. Any demand function can then be computed by the atrial device, which senses the endogenous ECG if present. In other embodiments, the atrial device is provided in a triggered mode in which each time it senses an atrial signal, it paces into that atrial signal (it will be in its refractory period at that point and can be used to alert the ventricular device that it needs to pace). This type of triggered pacing has been used in the past in other pacemaker systems because it was the only way people could tell that the pacemaker worked when the rates were adequate. Under this implementation of the invention, the ventricular device senses the atrial pacing spike during atrial sensing (since it was pacing into the atrial sensing) and, of course, during atrial pacing when the intrinsic atrial rate was too slow. In addition, in embodiments an accelerometer can be included to provide a rate modulation based on exercise and an "escape" algorithm in the ventricular device in case the atrial pulse fails. Such signaling, sensing, and rate modulation can be encoded into the electronics of the devices using routine efforts in the computer science field.

For many arrhythmias, it is useful to adjust or administer pacing only in response to the presence or absence of electrical signals generated by the heart. These electrical signals can be detected via the electrodes used for pacing or via separate electrodes. It is within the scope of this invention to include in the electronic circuitry such detection and control means as are well-known in the art of cardiac rhythm control. It is also within the scope of this invention to include the construction and deployment of two or more complete and separate devices in the same patient and the inclusion of communication means to permit exchange of data between those devices and/or with external devices, such as by wireless radio-frequency transmission or volume conduction through the intervening body tissues.

The step of contacting heart tissue typically involves movement, controlled by the practitioner, of the pacemaker system of the invention down a cannula placed in the patient's chest to effect physical contact of the tip of the electrode and the heart tissue. Contact can be confirmed by sense of touch, or visually using known techniques, such as ultrasound, X-ray imaging, or a camera. Typically, controlled movement of the system down the cannula is effected by holding the outside of the removable insertion casing and sliding it down the cannula. This can be accomplished through either direct contact between the practitioner and the removable insertion casing or indirect contact, such as through the use of a device designed for controlled insertion of the pacemaker system into a patient.

Implanting the electrode into the heart tissue can be accomplished by any act that physically and stably connects the electrode to the myocardial tissue. Numerous designs for cardiac pacemaker electrodes and electrode tips are known in the art, and any of those designs can be used in accordance with the present invention. However, it is recognized that an advantageous shape for use in the present invention is a corkscrew shape, which allows for implantation using an axial/rotational motion applied to the electrode by way of axial/rotational motion imparted to the removable insertion casing of the pacemaker system. It is to be understood that the present method, while applicable to endocardial approaches, does not require implanting the device through the venous system or implanting an electrode into a heart via endocardial tissue.

Once the electrode has been implanted into the heart tissue, and preferably after suitable pacing of the heart has been confirmed, the pacemaker is deployed in the patient's chest by disconnecting the pacemaker from the removable insertion casing. The step of disconnecting the two involves separating the removable insertion casing from the base element of the electrode sub-assembly. As discussed above, any number of mechanisms for connecting and disconnecting the two can be used. However, the most convenient and most cost-effective mechanism is by way of friction fit between the two. As such, in exemplary embodiments, the step of disconnecting the pacemaker from the removable insertion casing is performed by pushing the pacemaker with enough force to overcome the friction fit and eject the pacemaker from the removable insertion casing. As the pacemaker is located at the distal end of the removable insertion casing, it is necessary to use a push rod to expel it. The push rod can be provided as an element of the pacemaker system or can be provided separately.

Once the pacemaker has been disconnected from the removable insertion casing and deployed in the patient's chest, the removable insertion casing is removed from the patient's body by sliding it up through the cannula. The cannula then can be removed from the patient's body. The method thus provides a way to implant a pacemaker into a patient in which the entire pacemaker remains in the thoracic cavity.

The present invention includes, among other things, the following concepts:
  percutaneous anchoring of the electrode to the epicardial surface of the myocardium;
  deployment of the pacemaker in the thorax with a flexible lead to accommodate cardiac and respiratory motion;
  use of a novel but simple packaging scheme to achieve required longevity without bulky technologies;
  use of off-the-shelf electronic components to avoid expensive and risky custom development;
  minimize voltage and current requirements to maximize functional life without compromising pacing;
  ability to monitor charge-status of the implanted battery;
  inductive recharging system to extend functional life of the battery as needed; and
  scalability to provide appropriately sized pacemakers for patients of all sizes.

EXAMPLE

The invention will be further explained by the following Example, which is intended to be purely exemplary of the invention, and should not be considered as limiting the invention in any way.

A pacemaker with the mechanical features required for deployment according to the invention has been constructed and has been percutaneously implanted into an adult rabbit. The implantation was successful and showed the practicality of the device for in vivo use. The results provide compelling data regarding key aspects of the electronic and mechanical design strategies. Alteration of these aspects will be apparent to the skilled artisan as long as the effects are achieved.

Figure 2:
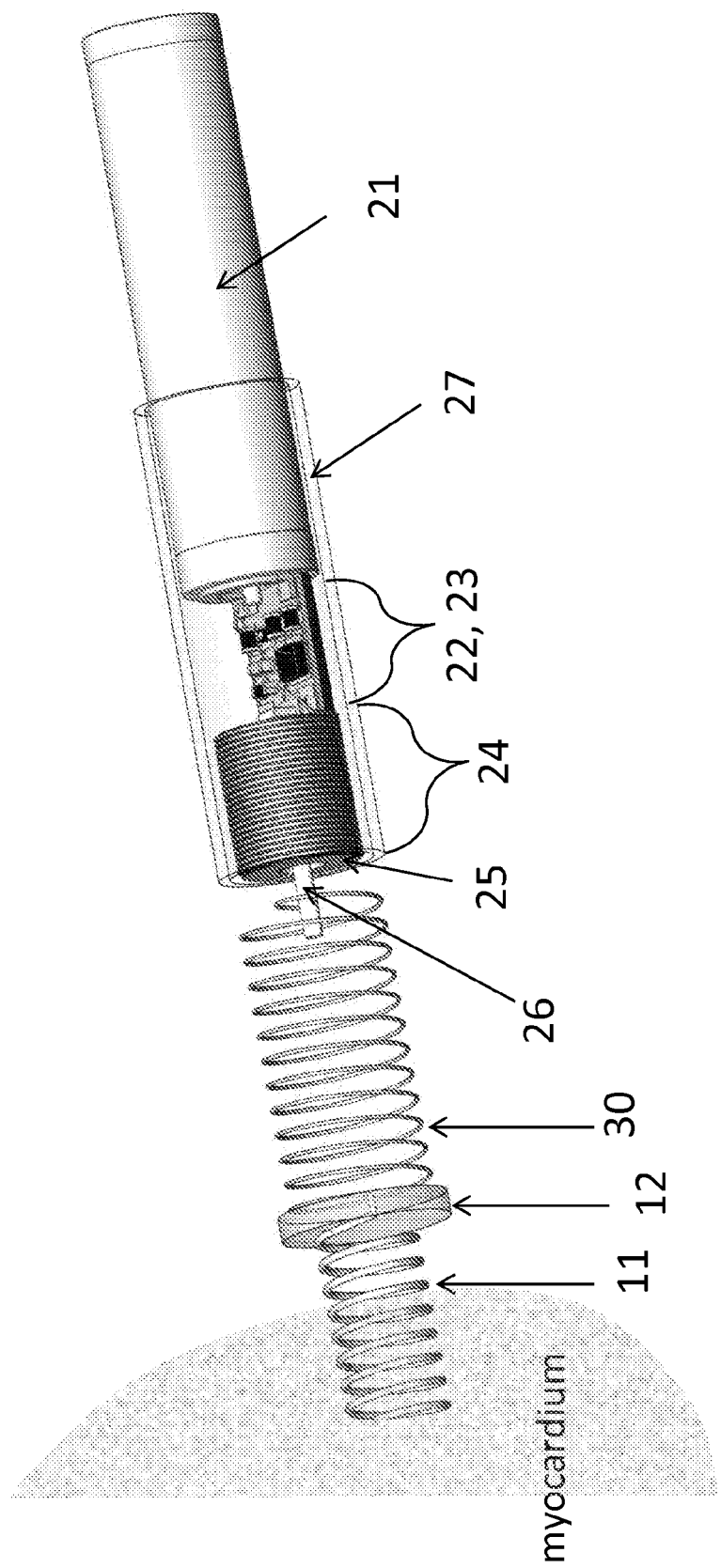
FIG. 2 shows the pacemaker of the embodiment of the invention depicted in FIG. 1 as it would look after deployment in a patient.

Mechanical Aspects:

The main mechanical challenge in arriving at the present invention was to integrate the power source, circuitry, electrode, and flexible lead into the size and form dictated by the 3.3 mm intra-uterine cannula typically used for the percutaneous implantation for fetal applications. While this size limit was not as challenging for larger devices, for example devices of up to 8 mm in diameter, overcoming the challenge for fetal applications enabled the fabrication of pacemakers for larger sized patients. FIG. 1 shows an embodiment of the functioning system, in which pacemaker 1 comprises electrode sub-assembly 10, implantable package 20, and lead 30. Electrode sub-assembly comprises electrode 11 and base 12. Implantable package 20 comprises power supply 21, electronic circuitry 22 on printed circuit board 23, coil 24 wound over ferrite 25, post 26, and water-impermeable shell 27. Flexible lead 30 physically and electrically connects electrode 11 to post 26. The Figure shows that pacemaker 1 is disposed within the interior space of removable insertion casing 40 that slips through the percutaneous operating cannula after the trocar is removed. The Figure further shows that base 12 of electrode sub-assembly 10 is wedged or otherwise friction-fit into the end of removable insertion casing 40 so that electrode 11, which has a corkscrew shape, can be screwed into the myocardium via its epicardial surface. The embodiment shown in the Figure has an open-ended distal end of the water-impermeable shell 27. Normally in such an embodiment, the airspace inside water-impermeable shell 27 would be filled with a water-resistant material, such as epoxy, to protect electronic circuitry 22 and printed circuit board 23 from body fluids. However, the water-resistant material is not shown in FIG. 1 (or FIG. 2, below) for viewing purposes. Similarly, in the embodiment shown, post 26 acts as both a connector between lead 30 and implantable package 20 and as a deployment spacer such that, when force is applied to the proximal end of power supply 21 by push rod 50, the force can be transmitted to base 12 without causing physical harm to flexible lead 30 (note that flexible lead 30 has spring-like qualities and compresses to a smaller size upon application of force). FIG. 2 shows the pacemaker of FIG. 1 after deployment in myocardial tissue. As can be seen from the Figure, removable insertion casing 40 has been removed.

Various electrode tapers and bevels were systematically tested for insertion force and mechanical stability in cadaver hearts before arriving at this design. The return electrode is the exposed metallic (in this example, titanium) case of power supply 21 (in this example, a lithium cell). Further, in this example, base 12 is an epoxy disk, electrode 11 is a 2 mm diameter corkscrew made from 0.006 inch pure iridium wire, and flexible lead 30 is 3 mm diameter spiral made from 0.003 inch diameter wire made of Pt-20Ir, and water-impermeable shell 27 is a borosilicate glass tube.

Electronic Aspects:

The main electronic challenge was to obtain the longest possible period of effective pacing within the limits of a tiny, off-the-shelf power supply, such as a lithium cell (e.g., Quallion QL0003I, Sylmar, Calif.), and conventional surface-mount components. We achieved this by using a relaxation oscillator that requires a single active component and delivers virtually all of its consumed power as stimulation pulses. The components on the left side of the schematic of FIG. 4 comprise the relaxation oscillator used in experiments. Output capacitor C is charged through resistor RC until its voltage reaches the threshold of the programmable uni-junction transistor (UJT) as defined by voltage divider R1 and R2. The UJT then switches to a low impedance state that allows all of the charge accumulated on C to discharge through the electrode (an equivalent circuit is a capacitor in series with a resistor). The UJT then switches back into a high impedance state and begins another charge/discharge cycle whose rate is defined by time-constant=RC*C. The component values in the schematic result in pulses that have a charge of approximately 1.5 μC and a rate of approximately 100 beats per minute, depending on the voltage of the power supply. Other pulse parameters are easily obtained by changing the values of the components, as is well-understood in the art. The components on the right comprise the inductive recharging and regulation system.

Electrochemical Aspects:

In order to provide sufficient pacing current despite the low available voltage, particular attention was paid to optimizing the electrode geometry, materials, and impedance. Testing showed that a suitable electrode can comprise a corkscrew shape having eight turns. In this exemplary embodiment, a thin layer (around 4 micrometers) of vapor-deposited Parylene-C protects the proximal five turns plus the flexible lead and the connection between them in the base. In this Example, the electrode and lead were physically and electrically connected prior to forming the base around the proximal end of the electrode. The distal three turns including the beveled cutting tip were masked during deposition, leaving them exposed. Iridium can be electrochemically activated by successive cyclic voltammetry cycles. This produces layers of conductive, porous iridium oxide that can absorb and release large amounts of charge (proportional to the enclosed area of the curves in the cyclic voltammogram). This effectively reduces the electrical impedance over the range of frequencies of interest to this application as a function of minutes of cyclic activation for such an electrode in saline. Activated iridium has the highest safety factor for electrical stimulation (3 $mC/cm^2$ charge density/phase) and is commonly used in modern cardiac pacing electrodes.

Figure 5:
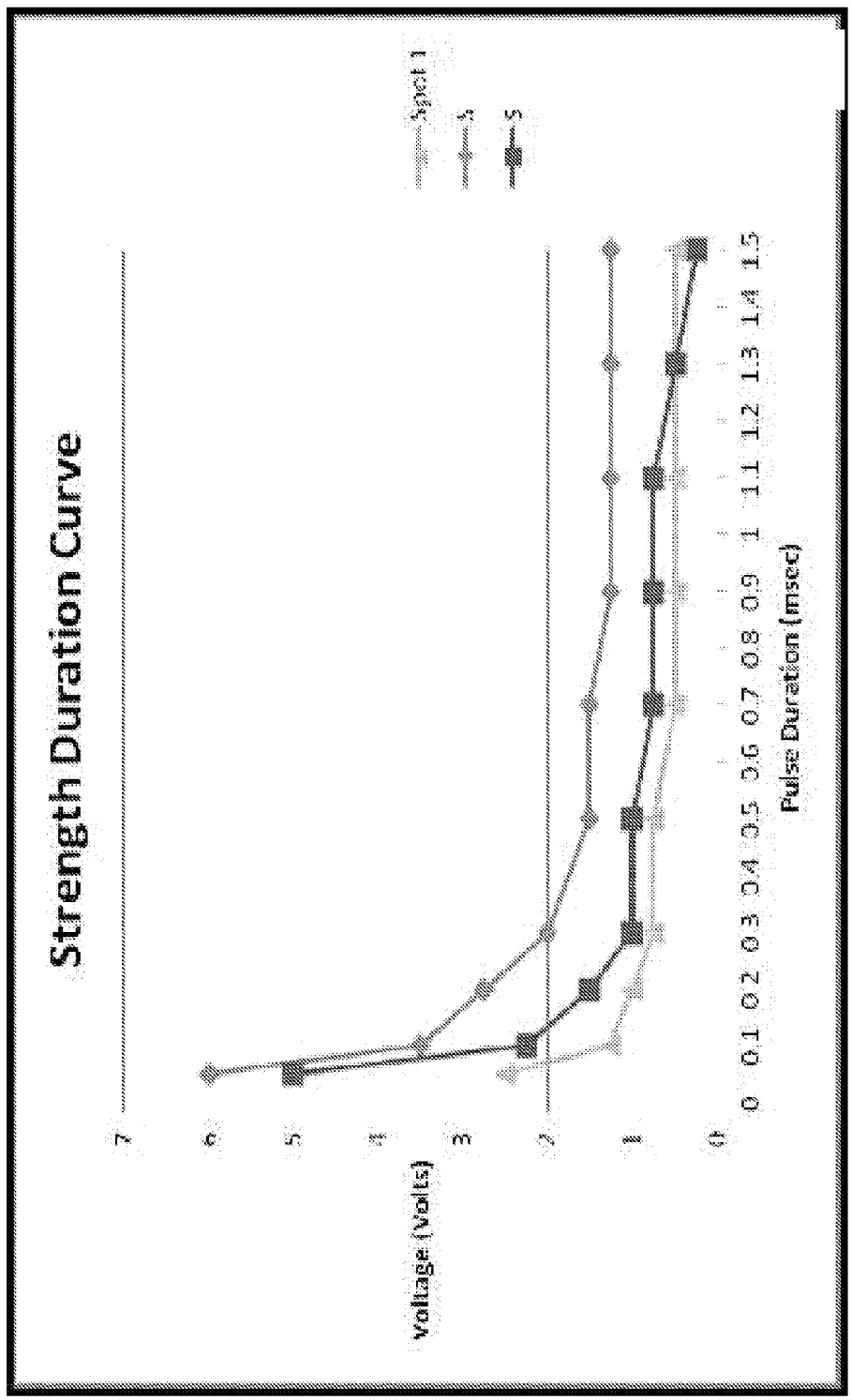
FIG. 5 shows strength-duration curves for three trials of a 1.2 mm diameter corkscrew electrode using a conventional squarepulse generator.

Thresholds for Pacing Capture:

Compelling data from implantation of a device according to the invention has been obtained from studies in adult rabbits. More specifically, a set of in vivo rabbit experiments was performed to establish mechanical and electrical specifications for a micro-pacemaker. A variety of sharpened iridium corkscrew electrodes (1.3 and 2.2 mm coil diameters) as part of a pacemaker of the invention were fabricated. Rabbit hearts were exposed via thoracotomy, and these test electrodes were implanted at various sites on the right and left ventricular epicardium in 3 rabbits. The test electrode was connected to an external and adjustable version of the pacemaker circuitry and measurements of capture thresholds, impedances, and sensed electrocardiograms were performed. These experiments allowed us to determine the required current and pulse duration of our pacing system and to identify the effects of electrode designs on mechanical insertion and electrical impedance. The smaller diameter (1.2 mm) coil provided the easiest and most reliable mechanical insertion of the electrode tip. As expected, the in situ impedance values were substantially higher in the open chest studies than in saline for all electrodes irrespective of size (around 600-1200Ω). The smaller coil electrodes had slightly higher impedance but slightly lower pacing thresholds, so voltage requirements were similar. The strength-duration curves for three insertions of a 1.2 mm diameter corkscrew electrode using a conventional squarepulse generator are plotted in FIG. 5. In a study by Assad et al., a strength duration curve was created using a different electrode design (T-bar shape without screw) in a 25-week hydropic human fetus at the time of implant and on the first postoperative day (POD). The fetus died by 36 hours after implantation of the lead (which was connected to a pacemaker in the maternal abdominal wall) and the electrode design was different from our screw mechanism, but their published strength-duration curve suggests a pacing threshold and chronaxie similar to our rabbit studies.

The relaxation oscillator produces an exponentially declining stimulus that does not provide explicit control of current or duration but does provide precise control of the pacing charge (and hence power consumption) by varying capacitor C. Importantly, the charge required to pace was substantially lower than anticipated. The chronaxie for a conventional square-wave stimulus is approximately 0.5 milliseconds (ms) and its effective charge lies between the total charge of the exponential pulse at infinity and the charge delivered at one time constant ($\tau$=0.375 ms). These relatively low charge values can be delivered through our low impedance electrodes using less than the nominal 3-4V DC available from the lithium cell, resulting in opportunities to increase battery life.

Percutaneous Delivery and Release:

The preliminary device implantation tools and techniques were piloted in a separate experiment, again using an in vivo rabbit model. A non-functional device with identical dimensions and mechanical features of our fetal micro-pacemaker was implanted into an adult rabbit percutaneously. A subxyphoid approach was used as well as the complete system for screwing the electrode into the beating myocardium and deploying the device in situ with its flexible lead. Using the identical trocar and cannula that would be used in a fetus, the device was implanted into the rabbit myocardium using ultrasound guidance and without surgical incisions. The animal was subsequently euthanized and we were able to confirm appropriate placement of the electrode in the myocardium with a favorable and safe position of the pacemaker and lead in the rabbit thorax. This result was extremely encouraging, as it confirmed the ability to implant the device percutaneously. Not only does this suggest the feasibility of implanting the device into a fetus, but it also demonstrates the ability to implant the pacing system into the thorax of an animal using only ultrasound guidance. This has immense potential for broadening the use of the system and the pacemaker to infants, children, and even adults, allowing for permanent pacemaker implantation without surgical incisions.

Battery Charger Concept

A commercially available rechargeable lithium cell from Quallion (QL000003I) has nominal voltage of 3.6V DC that varies between 3.0 and 4.0V DC depending on the level of charging. The relaxation oscillator that can be used in embodiments of the invention has a pacing rate that depends weakly on its supply voltage for most of that voltage range and then drops rapidly before ceasing to oscillate at around 2.4V DC. The pacing rate as a function of time since full charge is reproducible over many cycles of recharging. As such, one can determine the state of charge of the micro-pacemaker battery by tracking the exact pacing rate (readily determined from the electrical stimulus artifact rate on the maternal surface ECG). The pacemaker design allows for adjustment of battery life, with usual life being adjusted to two to three weeks per charge. The recharging system is based on recent advances in providing transcutaneous power to implanted electronic devices such as cochlear implants and spinal cord and neuromuscular stimulators via external and internal inductive coils that constitute a weakly coupled transformer. The external charger can consist of two major assemblies (Coil and Coil Driver) and a connecting coaxial cable. The charging Coil is approximately 40 cm in diameter and has a connection box that contains a resonating circuit. The Coil Driver is contained in a metallic enclosure and is grounded via the 120V AC connection that also powers the unit. The total power consumption of the system can be less than 30 Watts.

The Coil Driver contains four functional elements: i) medical-grade OEM 12V Power Supply, ii) voltage controlled oscillator (VCO), iii) Class-E amplifier, and iv) the Frequency Control for precise phasing of the high-Q, Class-E amplifier. The charging system operates at 6.78 MHz, which is a prescribed Industrial, Scientific, and Medical (ISM) frequency band. The FCC allows unlimited radiation within the prescribed ISM bandwidth of ±15 KHz (CFR 47 Part 18.305); at this frequency, human exposure is limited by thermal heating (IEEE C95.1-2005). The radiated RF power from the external charging system requires padding to mitigate possible tissue heating effects immediately adjacent to the coil as well as filtering to minimize out-of-band harmonics.

In the fetal embodiment, the recharging configuration is defined by the exciter/external coil to be placed over the abdomen of the mother (about 20 cm radius), the receiving/internal coil in the micro-pacemaker device (about radius of 1.5 mm, length of 6 mm) and the maximal distance between them (5-20 cm depending on the anatomy of the mother and the orientation of the fetus in the uterus. The implication of these values to the recharging time is understood. It is desirable to minimize the amount of time required to recharge the battery by applying the maximal recharging current to the battery that it can sustain without damage.

The design for the Class E oscillator described above has been simulated in PSPICE. One can use a combination of systematic simulation and breadboard construction and testing to optimize performance. Previous experience with similar inductive charging systems for the BION suggest that non-ideal behavior of electronic components is generally well-captured by their PSPICE models, but several factors must be tested empirically with actual circuitry and realistic conditions when modifying a given design, for example for use in a different patient population. These factors include the intervening conductive tissues of the body (which permit weak eddy currents that dissipate some energy) and varying orientations of the implant coil. The permittivity of the implant coil can be increased by winding it over a ferrite core, which improves the efficiency of power transmission and makes it less sensitive to orientation in the magnetic field. Additional components in the micro-pacemaker device are responsible for inductive capture of the RF energy and conversion into direct current to recharge the lithium cell battery. The exact design and values of the components COIL, RR, D1, and Z1 that constitute the charging and regulation circuitry can be varied by the skilled artisan using routine techniques without departing from the scope of the invention. However, it is to be understood that the entire system must function reliably over a very wide range of coupling coefficients as a result of uncertainties in the size of the mother's abdomen, the thickness of tissue overlying the uterus, and the position and orientation of the fetus within the uterus, which tends to change frequently.

Implant Development and Testing:

The size constraints and, in embodiments, RF recharging requirements, of preferred exemplary embodiments preclude, in some embodiments, the kinds of hermetic packaging that have become commonplace in implanted electronic pacemaker devices. However, hermetic packaging of electronic components is contemplated by the invention in some embodiments. The relatively short functional life of a pacemaker of the present invention, in embodiments, permits the use of water-resistant materials, alone or in combination with a water-impermeable material, to protect electronics of the pacemaker from exposure to water.

Figure 4:
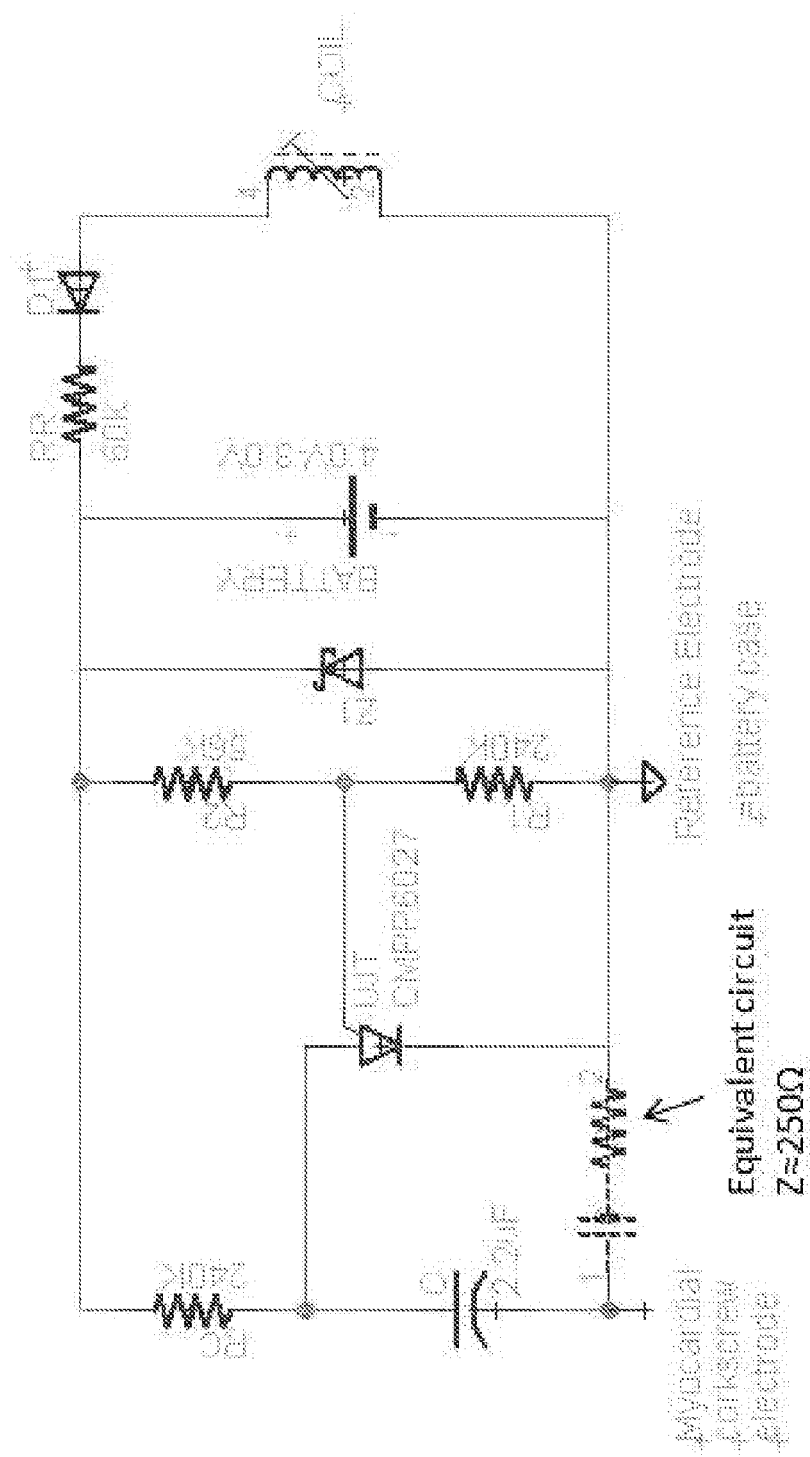
FIG. 4 shows an electronics schematic for an embodiment of the invention that includes an relaxation oscillator and an output capacitor.

The drawing in FIG. 1 shows all of the components of one embodiment of the pacemaker system of the invention, including the electronic components shown schematically in FIG. 4. Electronic circuitry 22 is located on and/or connected to printed circuit board 23, which rests on a shelf (not shown) in cylindrical ferrite 25 that holds receiving coil 24 for RF recharging and it is attached by laser welds and lead-free solder to the output pins of the lithium power supply 21. The relatively large output capacitor (not shown) is located within the lumen of ferrite 25 along with platinum post 26, where it is electrically and mechanically connected to flexible lead 30. Removable insertion casing 40 has a laser-cut perforation (not shown) to allow the titanium case of the lithium cell to function as the return electrode for pacing while the device is still in the surgical cannula (in order to assess adequate ventricular and/or atrial stimulation after electrode implantation but before deployment of the device).

A vacuum injection method can be used for creating a defect-free encapsulation of electronic circuitry and other electrical components (e.g., using a polymer) within water-impermeable shell 27, including the turns of receiving coil 24. Theory and experience have shown that water vapor diffusing through low-permeability polymers, such as epoxy, will eventually lead to circuit failure, but only when the water condenses on hydrophilic surfaces or in voids. The diffusion path to the active electronic components in the present pacemaker is long and narrow, but it is essential to maintain good chemical adhesion of the epoxy to all surfaces and to avoid bubbles during the injection process, particularly in the narrow gap between turns of coil 24. Procedures are known for out-gassing low-viscosity epoxies and using a combination of vacuum (to be applied to the battery end of shell 27) and pressurized monomer (to be applied to the coil end of shell 27) to achieve defect-free encapsulation. It is relatively easy to produce functional pacemakers using this construction that work reliably in vivo for substantially longer than the required maximal lifetime of 3 months, perhaps even for many years. Furthermore, a vacuum injection method can be used to force polymerizable material, such as monomers of an epoxy polymer or monomers of another polymeric adhesive, into the small gap between the inner surface of a water-impermeable shell and the outer surface of a power supply, thus forming a permanent attachment between the two and forming a water-resistant barrier.

It will be apparent to those skilled in the art that various modifications and variations can be made in the practice of the present invention and in construction of this device without departing from the scope or spirit of the invention. Other embodiments of the invention will be apparent to those skilled in the art from consideration of the specification and practice of the invention. It is intended that the specification and examples be considered as exemplary only.

The invention claimed is:

1. A minimally-invasive epicardial pacemaker system, said system comprising:
   a pacemaker comprising
      an electrode sub-assembly comprising an electrode and a base, wherein the base has a proximal surface, a distal surface, and an outer surface defining a cross-sectional shape, and wherein the electrode extends from the distal surface of the base,
      an implantable package with electronic circuitry and a power supply, and
      a flexible, electrically conductive lead extending from the proximal surface of the base and connecting the electrode to the implantable package; and
   a removable insertion casing directly contacting at least a portion of the base of the electrode sub-assembly, wherein contact between the inner surface of the removable insertion casing and the outer surface of the base causes deformity of the removable insertion casing, the base, or both, and wherein said contact provides sufficient physical connection between the insertion casing and the base to permit an operator to apply axial motion to the electrode via force applied to the insertion casing.

2. The pacemaker system of claim 1, wherein the electrode of the electrode subassembly comprises a corkscrew shape.

3. The pacemaker system of claim 1, wherein the electrode of the electrode subassembly comprises iridium.

4. The pacemaker system of claim 1, wherein the base of the electrode sub-assembly comprises epoxy.

5. The pacemaker system of claim 1, wherein the electronic circuitry of the implantable package comprises electronic components for providing controlled electrical pulses from the pacemaker to a patient's heart.

6. The pacemaker system of claim 1, wherein the cross-sectional shape defined by the inner surface of the removable insertion casing is different than the cross-sectional shape defined by the outer surface of the base such that the inner surface of the removable insertion casing and the outer surface of the base make contact at some, but not all, points on their respective surfaces.

7. The pacemaker system of claim 6, wherein the inner surface of the removable insertion casing has a circular shape and the outer surface of the base has a polygonal shape with vertices that contact the inner surface of the removable insertion casing.

8. The pacemaker system of claim 1, wherein the cross-sectional geometric shape of the base of the electrode sub-assembly and the cross-sectional geometric shape of the insertion casing are the same shape, which are either circular or non-circular, and wherein contact between the base and insertion casing creates a friction fit between the two.

9. The pacemaker system of claim 1, wherein the power supply of the implantable package comprises a lithium ion power cell.

10. The pacemaker system of claim 1, wherein the implantable package further comprises components for receiving power from an external source.

11. The pacemaker system of claim 10, wherein the implantable package comprises a receiving coil for radio frequency recharging of the device.

12. The pacemaker system of claim 1, further comprising a water barrier that protects the electronic circuitry from damage by water.

13. The pacemaker system of claim 12, wherein the water barrier comprises a water impermeable shell that covers a portion of the power supply and all of the electronic circuitry.

14. The pacemaker system of claim 13, wherein the water barrier further comprises a water-resistant material that coats the electronic circuitry.

15. The pacemaker system of claim 1, wherein the removable insertion casing has an outer diameter or width of 3.3 mm or less.

16. The pacemaker system of claim 1, wherein the removable insertion casing has an outer diameter or width of 3 mm to 12 mm.

17. A process for making a minimally invasive cardiac pacemaker system, said process comprising physically connecting
   A) a pacemaker having an electrode sub-assembly comprising i) an electrode and a base that encases a part of the electrode, the base being defined by a distal surface, a proximal surface, and an outer surface, and wherein the electrode extends from the distal surface of the base, ii) a flexible, electrically conductive lead extending from the proximal surface of the base, and iii) an implantable package with a power supply and electronic circuitry for controlling the pacing of the pacemaker, wherein the flexible lead connects to the electronic circuitry at the proximal side of the base, to B) a removable insertion casing, the casing being defined by a distal surface, a proximal surface, an inner surface, and an outer surface, by physically contacting the inner surface of the removable insertion casing and the outer surface of the base, wherein contact between the inner surface of the removable insertion casing and the outer surface of the base causes deformity of the removable insertion casing, the base, or both, and wherein said contact provides sufficient physical connection between the removable insertion casing and the base to permit an operator to apply axial or rotational motion to the electrode via force applied to the removable insertion casing.

18. The process of claim 17, further comprising inserting a push rod into the removable insertion casing such that one end of the push rod contacts the power supply and the other end of the push rod extends outside of the removable insertion casing.

19. The process of claim 17, further comprising introducing a hole through the inner and outer surfaces of the removable insertion casing to allow for conduction of electricity between the lumen and exterior of the removable insertion casing.

20. The process of claim 19, wherein the inner surface of the removable insertion casing and the outer surface of the base are caused to make contact at some, but not all, points on their respective surfaces.

21. The process of claim 17, wherein the inner surface of the insertion casing defines a cross-section having a different geometrical shape than the outer surface of the base.

* * * * *